US012702702B2

(12) United States Patent
Liu et al.

(10) Patent No.: US 12,702,702 B2
(45) Date of Patent: Aug. 11, 2026

(54) APPLICATION OF CAERIN 1.1/1.9 COMBINED WITH ANTI-CD47 ANTIBODY IN PREPARING DRUG FOR TREATING MELANOMA

(71) Applicants: WNL BIOMED TECH PTY. LTD., Brisbane (AU); Zhong'ao Biomedical Technology (Guangdong) Co., Ltd, Zhongshan (CN)

(72) Inventors: Xiaosong Liu, Brisbane (AU); Junjie Li, Zhongshan (CN); Guoying Ni, Brisbane (AU); Tianfang Wang, Brisbane (AU)

(73) Assignees: WNL BIOMED TECH PTY. LTD., Brisbane (AU); Zhong'ao Biomedical Technology (Guangdong) Co., Ltd, Zhongshan (CN)

( * ) Notice: Subject to any disclaimer, the term of this patent is extended or adjusted under 35 U.S.C. 154(b) by 0 days.

(21) Appl. No.: 19/216,450

(22) Filed: May 22, 2025

(65) Prior Publication Data

US 2025/0288656 A1 Sep. 18, 2025

Related U.S. Application Data

(63) Continuation of application No. PCT/CN2023/121936, filed on Sep. 27, 2023.

(30) Foreign Application Priority Data

Nov. 22, 2022 (CN) ......................... 202211465805.4

(51) Int. Cl.

*A61K 39/00* (2006.01)
*A61K 38/17* (2006.01)
*A61K 39/395* (2006.01)
*A61P 35/00* (2006.01)

(52) U.S. Cl.

CPC .... *A61K 39/00119* (2018.08); *A61K 38/1729* (2013.01); *A61K 39/3955* (2013.01); *A61K 39/39558* (2013.01); *A61P 35/00* (2018.01)

(58) Field of Classification Search

None

See application file for complete search history.

(56) References Cited

U.S. PATENT DOCUMENTS

2019/0248915 A1* 8/2019 Chao ...................... C07K 16/30
2019/0374603 A1 12/2019 Wang et al.

FOREIGN PATENT DOCUMENTS

CN 114437182 A 5/2022

OTHER PUBLICATIONS

E.g., Almagro & Fransson, Frontiers in Bioscience 2008; 13:1619-33 (Year: 2008).*

Gershoni et al., Epitope Mapping, Biodrugs 2007; 21 (3): (Year: 2007).*

Blythe et al., Benchmarking B cell epitope prediction: Underperformance of existing methods, Protein Science (2005), 14:246-248 p. 246) (Year: 2005).*

Schreiber et al.,3D-Epitope-Explorer (3DEX): Localization of Conformational Epitopes within Three-Dimensional Structures of Proteins, Wiley Interscience, 2005 42-44, (Year: 2005).*

Wilde et al (Blood (2025) 145 (5): 460â462) (Year: 2025).*

Xu et al (Front Immunol. Feb. 23, 2024;15:1348852) (Year: 2024).*

Gracia-Grijo et al. (Frontiers in Immunology 2019 10 1-19) (Year: 2019).*

Hu et al (Nature Reviews Immunology 2018 18, 168-182) (Year: 2018).*

Title of the Item: Proc Natl Acad Sci USA Publication Date: Apr. 18, 2016 Name of the Author: Jonathan T Sockolosky et al.Article Title: Durable antitumor responses to CD47 blockade require adaptive immune stimulation pp. E2646-E2654.

Title of the Item: Clinical Translational Immunology Publication Date: Aug. 17, 2021 Name of the Author: Guoying Ni et al.Article Title: Intratumoral injection of caerin 1.1 and 1.9 peptides increases the efficacy of vaccinated TC-1 tumor-bearing mice with PD-1 blockade by modulating macrophage heterogeneity and the activation of CD8 T cells in the tumor.

* cited by examiner

*Primary Examiner* — Zachariah Lucas
*Assistant Examiner* — Sarah A Alsomairy
(74) *Attorney, Agent, or Firm* — Nitin Kaushik

(57) ABSTRACT

The present invention belongs to the field of biotechnology, and particularly relates to an application of Caerin 1.1/1.9 combined with an anti-CD47 antibody in preparing a drug for treating melanoma. In the present invention, an amino acid sequence of the Caerin 1.1 is shown in SEQ ID NO.1; and an amino acid sequence of the Caerin 1.9 is shown in SEQ ID NO.2. The Caerin 1.1/1.9 of the present invention may promote B16 cells to highly express CD47 while leading to apoptosis of the B16 cells, promote macrophages to phagocytose tumor cells in the presence of anti-CD47 antibodies, improve the curative effect of the Caerin 1.1/1.9, which is also superior to that of a single anti-CD47 antibody, and lays a foundation for expanding the application of CD47 inhibition/blocking drugs.

6 Claims, 16 Drawing Sheets

Specification includes a Sequence Listing.

A.

B.

%CD3+ in CD45.2+ cells
6
4
2
0
ns
***
**
CD3+

C.

D.

E.

F.

G.

PBS
P3
F1/F3

SEQUENCE LISTING

```
Sequence total quantity: 2
SEQ ID NO: 1            moltype = AA  length = 29
FEATURE                 Location/Qualifiers
source                  1..29
                        mol_type = protein
                        organism = synthetic construct
SEQUENCE: 1
GLLSVLGSVA KHVLPHVLPH VVPVIAEHL                                    29

SEQ ID NO: 2            moltype = AA  length = 25
FEATURE                 Location/Qualifiers
source                  1..25
                        mol_type = protein
                        organism = synthetic construct
SEQUENCE: 2
GLFGVLGSIA KHVLPHVVPV IAEKL                                        25
```

APPLICATION OF CAERIN 1.1/1.9 COMBINED WITH ANTI-CD47 ANTIBODY IN PREPARING DRUG FOR TREATING MELANOMA

CROSS-REFERENCE TO RELATED APPLICATIONS

The application claims priority to Chinese patent application No. 202211465805.4, filed on Nov. 22, 2022, the entire contents of which are incorporated herein by reference.

SEQUENCE LISTING

The sequence listing xml file submitted herewith, named "SeqList.xml", created on May 14, 2025, and having a file size of 2,728 bytes, is incorporated by reference herein.

TECHNICAL FIELD

The present invention belongs to the field of biotechnology, and particularly relates to an application of Caerin 1.1/1.9 combined with an anti-CD47 antibody in preparing a drug for treating melanoma.

BACKGROUND

Malignant melanoma is a tumor produced by melanocytes of skin and other organs. Cutaneous melanoma is characterized by obvious changes in pigmented skin lesions over months or years. Although the incidence of the disease is low, it has high malignancy, early metastasis, and high mortality, so that early diagnosis and treatment are very important. The malignant melanoma mostly occurs in adults, and cases of secondary carcinogenesis of giant congenital melanocytic nevus are more common in children. Because melanoma is extremely harmful to human bodies, its treatment has always been concerned by all walks of life.

Immunotherapy is a new method for tumor treatment. Immune checkpoint inhibitors such as anti-PD1 and anti-CTLA4 have been widely used in clinic. With the continuous development and progress of scientific research, new immune checkpoints are continuously discovered, such as anti-CD47. But there is a common problem in the actual use of these immune checkpoints. Because these immune checkpoints can induce apoptosis of tumor cells, macrophages are affected and cannot phagocytose the tumor cells, and finally a tumor immune microenvironment is destroyed, so that the efficiency of the immunotherapy is limited.

Caerin 1 polypeptide family is an antibacterial polypeptide secreted by skin of Litoria caerulea, including Caerin 1.1, Caerin 1.9, etc., and has antibacterial and anti-tumor cell growth activity. Researches show that Caerin 1.1 and Caerin 1.9 may inhibit the growth of human and mouse cervical cancer cells, human thyroid cancer cells, and human breast cancer cells in vitro, and induce Hela cell apoptosis through a TNFalpha signal conduction path. Coupling nuclide may improve its anti-tumor efficiency. The growth of TC-1 cells may be inhibited in vivo and blood cells such as T cells, NK cells, and the like are attracted to tumor tissues. However, these only prove that Caerin 1.1 and Caerin 1.9 may inhibit tumors and do not change the above-mentioned problems. Furthermore, there is no report about the application of Caerin 1.1 and Caerin 1.9 in treating melanoma in the prior art.

In conclusion, the prior art generally has the technical problems that the tumor immune microenvironment is destroyed, the immunotherapy efficiency is influenced, the application range of Caerin 1.1 and Caerin 1.9 is narrow, and the like in the treatment process.

SUMMARY

In view of the problems generally existing in the prior art, the present invention provides an application of Caerin 1.1/1.9 combined with an anti-CD47 antibody in preparation of a drug for treating melanoma. The three components are combined to prepare a drug for treating melanoma, so that the immunotherapy effect is improved.

To achieve the above objectives, a technical effect adopted by the present invention is:

an application of Caerin 1.1/1.9 combined with an anti-CD47 antibody in preparing a drug for treating melanoma.

Preferably, a mass ratio of Caerin 1.1/1.9 to the anti-CD47 antibody (clone: MIAP301) is 3:(10-25) (i.e., 60 μg:200 to 500 μg/mouse).

The dosage of the anti-CD47 antibody added to a mouse is 200 to 500 μg/mouse, and the adding dosage of Caerin 1.1/1.9 is 60 μg/mouse, where a mass ratio of Caerin 1.1 to Caerin 1.9 is 1:1, i.e., adding 30 μg/mouse each.

Preferably, an amino acid sequence of Caerin 1.1 is shown in SEQ ID NO.1; and an amino acid sequence of Caerin 1.9 is shown in SEQ ID NO.2.

```
                                    (SEQ ID NO. 1)
GLLSVLGSVAKHVLPHVLPHVVPVIAEHL-NH2;

                                    (SEQ ID NO. 2)
GLFGVLGSIAKHVLPHVVPVIAEKL-NH2;
```

The present invention further provides an application of Caerin 1.1/1.9 in inducing melanoma cells B16 to express CD47 in a large quantity.

Preferably, the drug further includes a pharmaceutically acceptable carrier.

The present invention further provides an application of Caerin 1.1/1.9 in preparing a pharmaceutical composition for treating tumors.

Preferably, the pharmaceutical composition further includes an anti-CD47 antibody and a therapeutic vaccine.

Preferably, the therapeutic vaccine consists of a melanoma therapeutic vaccine, MPLA, and α-IL10r.

Preferably, the tumor is melanoma or cervical cancer.

A mechanism research shows that Caerin 1.1/1.9 improves the tumor immune microenvironment, and re-polarizes tumor infiltrating macrophages, so as to convert the tumor infiltrating macrophages from an M2 type to an M1 type. More interleukin 12 and less interleukin 10 are secreted. If the therapeutic vaccine contains a melanoma therapeutic vaccine and an interleukin 10 inhibitory antibody, combination use of Caerin 1.1/1.9 and them can inhibit the growth of TC-1 cells more effectively. The combination use of Caerin 1.1/1.9, the anti-CD47 antibody, and the therapeutic vaccine may eliminate tumor completely in 20-50% of TC-1 tumor-bearing mice.

The inventors found that Caerin 1.1/1.9 inhibited the growth of melanoma B16 cells in vitro, induced apoptosis of melanoma B16 cells, and could enter into B16 cells, so as to inhibit the growth of B16 cells in vivo. The high expression of CD47 by the B16 cells improves the efficiency of the anti-CD47 antibody in a B16 model, attracts blood cells to tumors, particularly macrophages and CD4+T cells to the tumors, so that the macrophages phagocytose the tumor cells. When combined with the anti-CD47 antibody and the therapeutic vaccine, tumors of 50% of tumor-bearing mice may be completely eliminated.

Compared with the prior art, the technical solution of the present invention has the following advantages: the present invention solves the curative effect problem of the anti-CD47 in melanoma, induces B16 cells to highly express CD47, and improves the curative effect of treating the B16 tumor by combined use of the anti-CD47 and Caerin 1.1/1.9. The triple therapy of the anti-CD47, the therapeutic vaccine, and the Caerin 1.1/Caerin 1.9 may achieve better effect of treating the B16 tumor than that when an α-PD-1 is used.

DETAILED DESCRIPTION OF THE EMBODIMENTS

The present invention is further explained below in conjunction with embodiments, but it should be noted that the following embodiments are only used to explain rather than limit the present invention, and all technical solutions identical or similar to the present invention fall within the protection scope of the present invention. Where no specific techniques or conditions are specified in the embodiments, operations are performed according to conventional technical methods and content of instrument specifications in the art; and where no manufacturers are specified for reagents or instruments used herein, they are all conventional products that are commercially available.

Experiment Example 1 In Vitro Detection Experiment

I. Experimental Process:

1. An MTT assay was used to detect cell survival condition: $7\times10^4$ B16 cells per well were cultured overnight with F1/F3 at different concentrations (0, 6, 8, 10, 12, 14, 16, 18, 20 μg/mL) in 4 duplicate wells, and the cell survival condition was detected by using an MTT kit (a product number: C0009M) and an IC50 value was calculated by drawing. Latest results of two independent experiments were shown.
2. Detection of cell apoptosis: it was divided into a test group and a control group, and the B16 cells were cultured with a complete medium (composed of 1640 basic medium+fetal bovine serum from South American+double antibody (mixed with penicillin and streptomycin at a ratio of 1:1) at a volume ratio of 90:9:1), where Caerin 1.1/Caerin 1.9 was added to the test group with a final concentration of 10 μg/mL, and P3 was added to the control group with a same final concentration of 10 μg/mL. The cells were cultured overnight in a 5% $CO_2$ incubator at 37° C., and their apoptosis conditions were detected by an apoptosis kit (an Annexin V-EGFP apoptosis detection kit, with a product number: C1067M).

Figure 1:
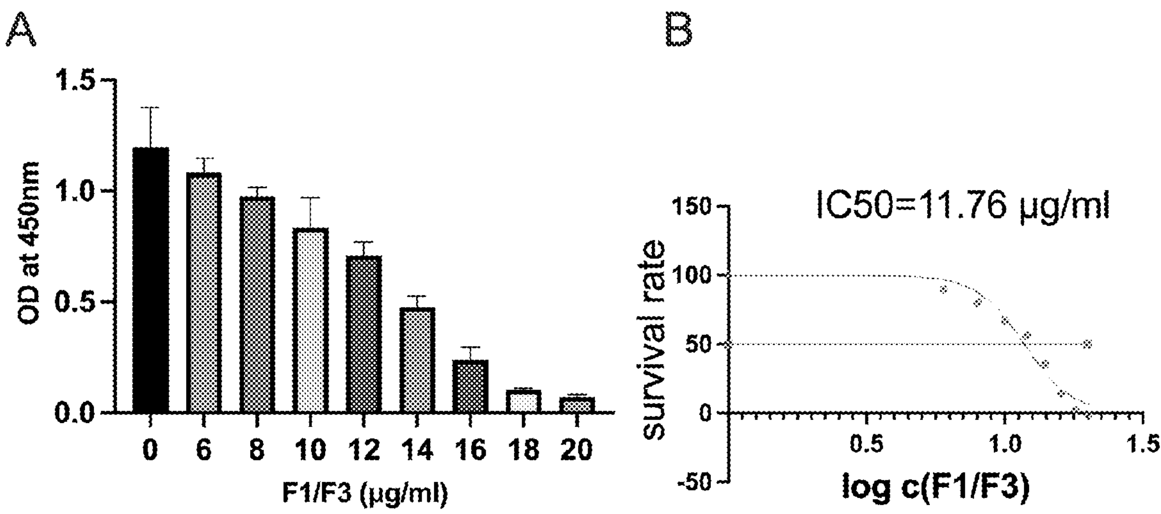
FIG. 1 shows a result of MTT assay for detecting cell activity.
Figure 2:
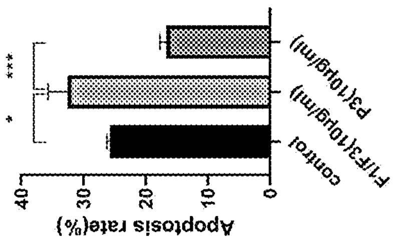
FIG. 2 shows a result of apoptosis detection and shows a result of promoting the increase of CD47 by combined use of F1/F3.
Figure 2:
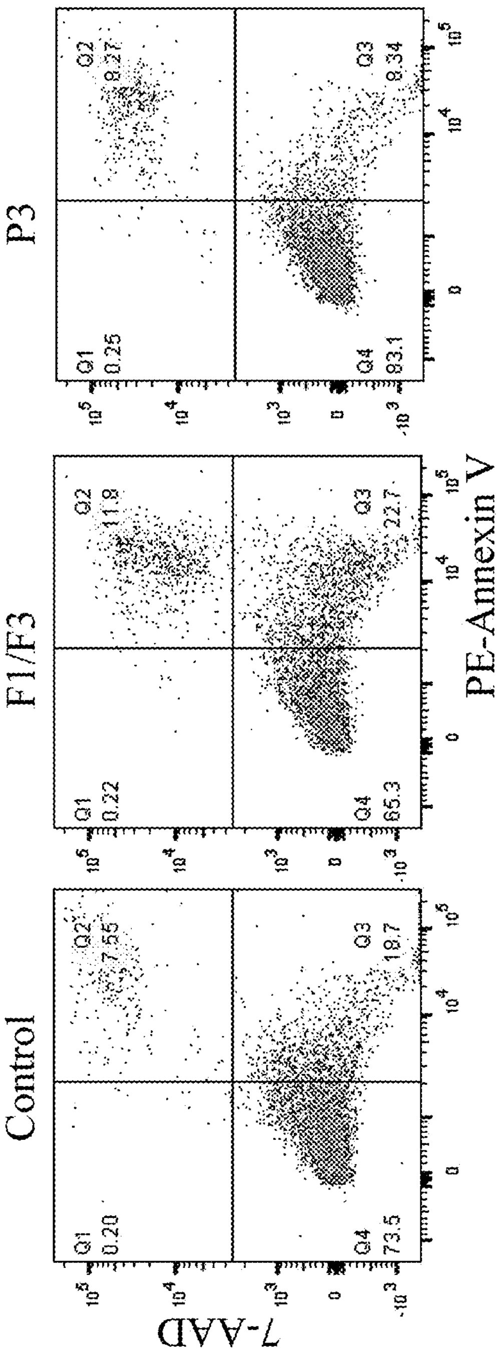

II. Experimental Results:

1. The cell survival condition was shown in FIG. 1. In FIG. 1, A represented the cell survival condition at different concentrations, and B represented a calculated survival rate. It may be seen from FIG. 1 that $IC_{50}$ ($IC_{50}$ half lethal dose)=11.76 μg/mL, and Caerin 1.1/Caerin 1.9 can obviously inhibit the proliferation of the B16 cells.
2. Cell apoptosis condition was shown in FIG. 2. In FIG. 2, A was a cell apoptosis distribution diagram, and B was a statistical analysis result. It may be seen that it had a significant apoptosis-inducing effect on B16 at 10 μg/mL.

Experiment Example 2 In Vivo Detection Experiment

1. Experiment objects: 12 C57BL/6 mice were divided into 3 groups with 4 mice in each group.
2. Experiment method:

2.1 Detection of tumor weight: A. Each C57BL/6 mouse was subcutaneously inoculated with $4\times10^5$ B16 cells, and time of tumor bearing was recorded as DAY 0. On DAY 3, the three groups were respectively injected with 100 μL of PBS solution containing 30 μg of F1/F3 (i.e., Caerin 1.1/Caerin 1.9), 100 μL of PBS solution containing 30 μg of P3, and 100 μL of PBS solution for the negative control group every day, administered for 7 consecutive days; B. a modeling method was the same as above, there were 8 mouse in each group, which were killed at DAY 13, and the tumor was taken and weighed.

2.2 Detection of cell activity: The experimental process was the same as that in 2.1, tumor tissues were taken and treated into single cell suspensions on DAY 13 for flow staining and detected by using a flow cytometer, and selected flow antibodies were as follows: FITC-CD45.2, APC-cy7-CD3e, Percp-cy5.5-CD4, PE-cy7-CD8a, APC-cy7-B220, PE-NK1.1, PE-F4/80, Percp-cy5.5-CD11b, and FVS510 dye. Changes of macrophage subtypes were detected, tumor tissues were taken and treated into single cell suspensions on DAY 13 for flow staining and detected by using the flow cytometer, and selected flow antibodies were as follows: FITC-CD45.2, PE-F4/80, Percp-cy5.5-CD11b, BV421-Ly6C, and FVS510 dye.

Figure 3:
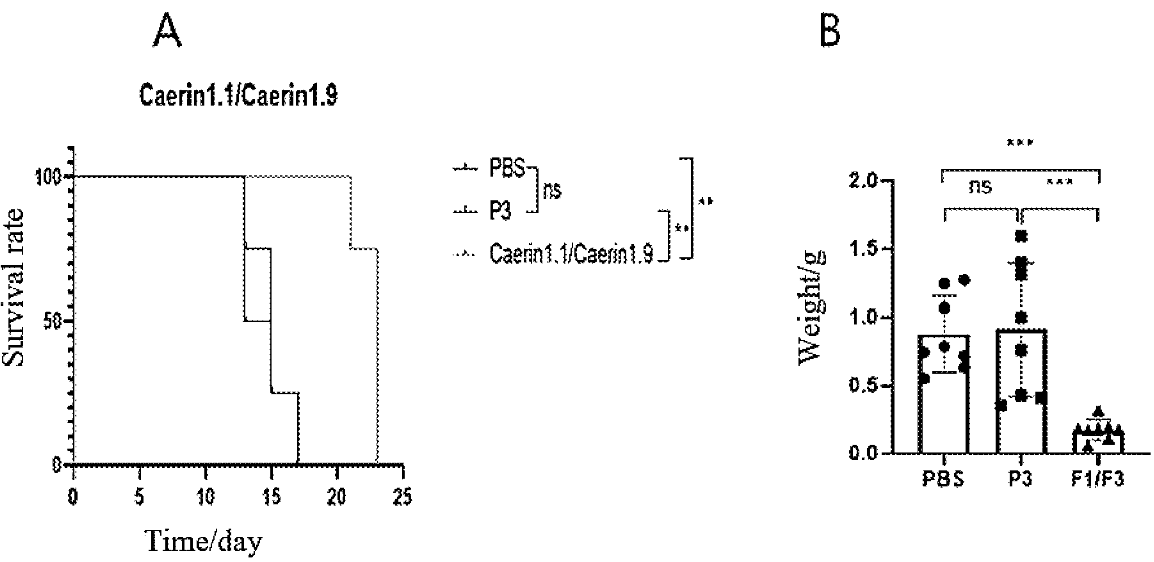
FIG. 3 shows a result of survival time and tumor weight of F1/F3 combined intratumoral injection therapy.

3. Experimental results:

3.1 The experimental results were shown in FIG. 3. In FIG. 3, A was the survival time of Caerin 1.1/Caerin 1.9 for combined treatment of melanoma-bearing mice, and B was weighted data of tumor size of each group. It may be seen from the figure that Caerin 1.1/Caerin 1.9 alone can effectively inhibit tumor growth in vivo.

Figure 4:
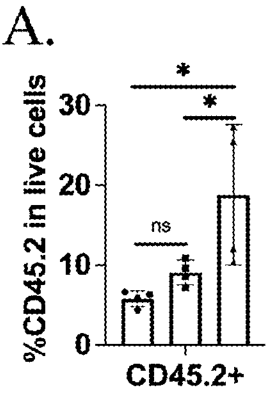
FIG. 4 shows a comparison result of cell activity marked by different antibodies.
Figure 4:
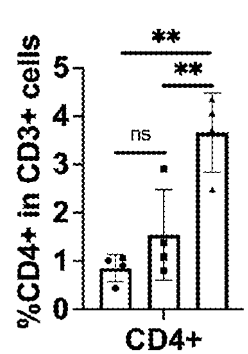
Figure 4:
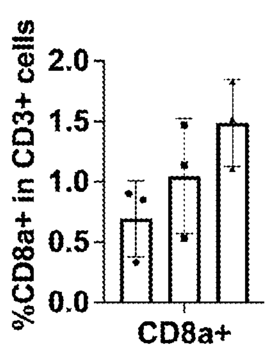
Figure 4:
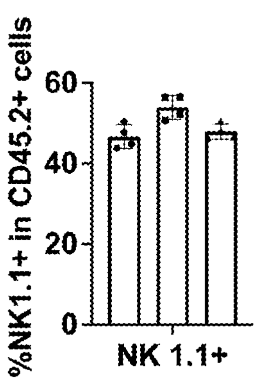
Figure 4:
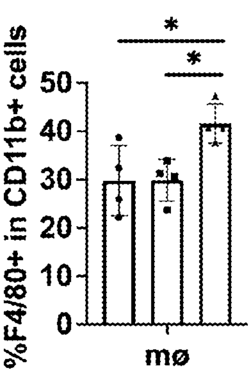
Figure 4:
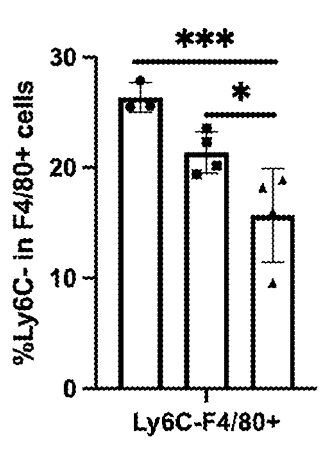
Figure 4:
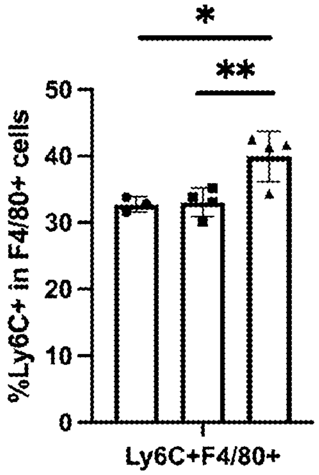

3.2 Results of the cell activity detection experiment were shown in FIG. 4, and meanings of A to G in FIG. 4 were as follows: A represented a proportion of CD45+cells in living cells; B represented a proportion of CD3+cells in CD45+cells; C represented a proportion of CD4+cells in CD45+cells; D represented a proportion of CD8+ cells in CD3+cells; E represented a proportion of NK1.1+cells in CD45.2+cells; F represented a proportion of macrophages in CD45.2+cells; and G represented a proportion of macrophage subtypes in macrophages and the cell activity under different antibodies. From this, it can be seen that the number of CD8+T cells and CD4+T cells increased, the number of macrophages increased; the number of inflammatory macrophages for promoting tumor immunity increased, the number of tissue-resident macrophages for inhibiting tumor immunity decreased, the expression of INFα receptors in macrophages increased, and the expression of receptors in subtype macrophages increased, which indicated that: after polypeptide therapy, "cold tumor" was converted into "hot tumor", and it was suggested that the inhibitory effect of the polypeptide on tumor growth was closely related to macrophages and INFα.

Experiment Example 3 Detection of Tumor Smearing Therapy

Figure 5:
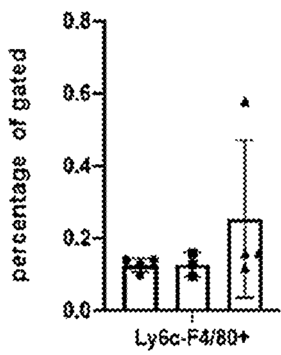
FIG. 5 shows a result of a tumor smearing detection experiment.
Figure 5:
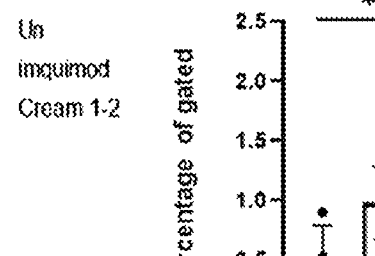
Figure 5:
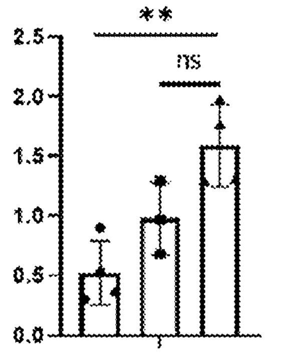

1. Experiment objects: 12 C57BL/6 mice were divided into 3 groups with 4 mice in each group.
2. Experimental process: Each C57BL/6 mouse was subcutaneously inoculated with $4\times10^5$ B16 cells, and time of tumor bearing was recorded as DAY 0. Mice were divided into three groups on DAY 3: a UN group (without any treatment), an imquimod group, and an F1/F3 Cream 1-2 group. A smearing experiment was started on DAY 3, and 1% pentobarbital was injected intraperitoneally before smearing, for the imquimod group: imquimod ointment was evenly applied to the tumor surface until the tumor was just covered, once every other day until DAY 11, and for the F1/F3 cream 1-2 group: F1/F3 ointment was evenly applied on the tumor surface until the tumor was just covered, twice a day for continuously smearing 9 days. Tumor tissues were taken and treated into single cell suspensions on DAY 12 for flow staining and detected by using a flow cytometer. Selected flow antibodies were as follows: FITC-CD45.2, PE-F4/80, Percp-cy5.5-CD11b, BV421-Ly6c, and FVS510 dye.
3. Experimental results: Specific experimental results were shown in FIG. 5. In FIG. 5, a left figure shows a result of changes in the number of macrophages in each group, and a right figure shows a result of changes in the number of inflammatory macrophages. It can be seen from FIG. 5 that the changes of macrophage subtypes were basically the same after polypeptide treatment in different dosage forms, which indicates that the conclusion that F1/F3 for treatment of melanoma is related to macrophages is reliable.

Figure 6:
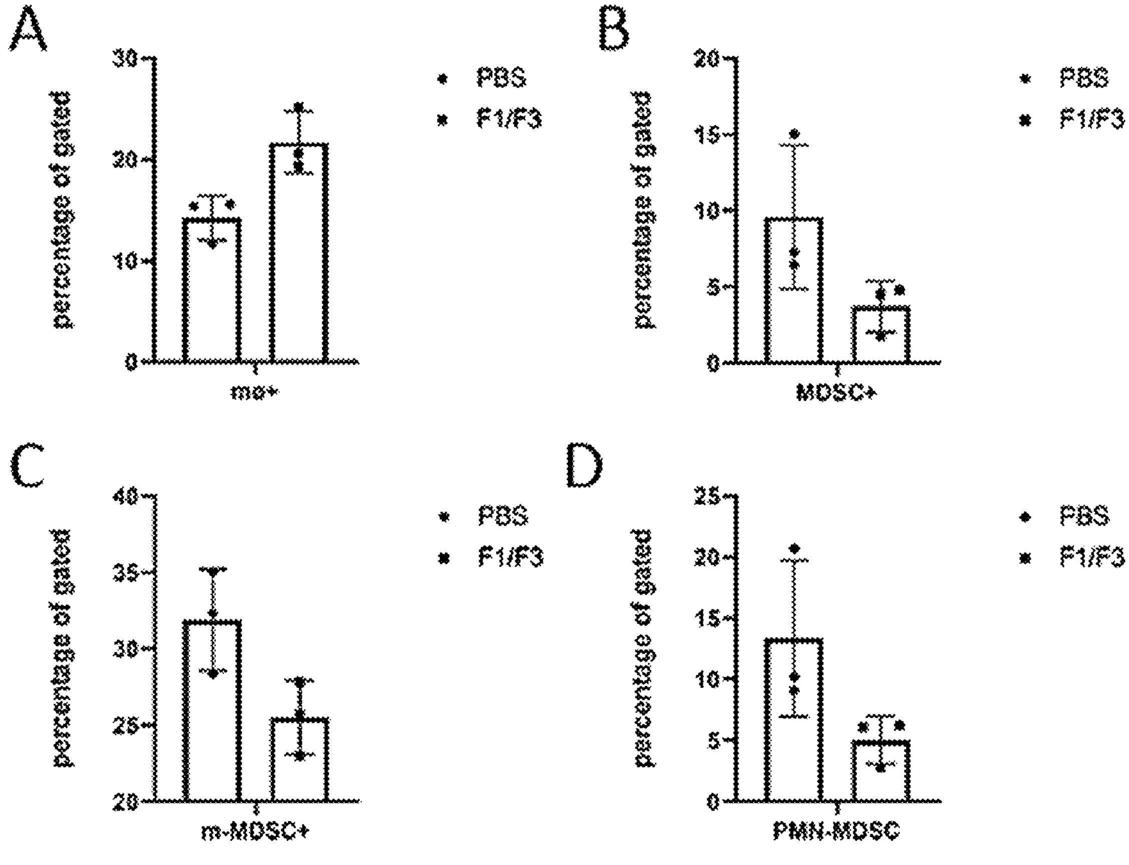
FIG. 6 shows a result of conversion of MDSC into macrophages by F1/F3 combined therapy.
Figure 7:
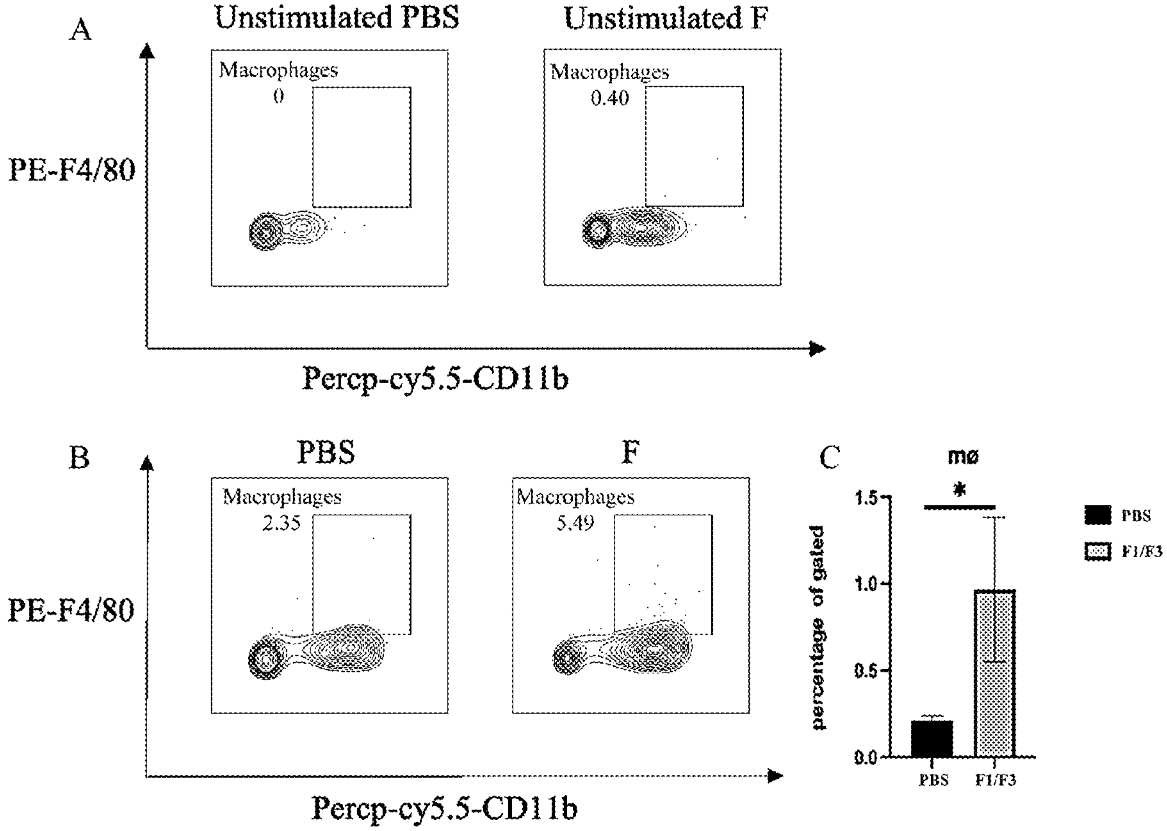
FIG. 7 shows a result of a sorting in vitro stimulation culture experiment.

Experiment Example 4 F1/F3 For Combined Treatment of Conversion of MDSC Into Macrophages 1. Experiment objects: 6 C57BL/6 mice were divided into 2 groups with 3 mice in each group.
2. Experimental process: Each C57BL/6 mouse was subcutaneously inoculated with $4\times10^5$ B16 cells, and time of tumor bearing was recorded as DAY 0. The two groups were injected with 100 μL of PBS solution containing 30 μg of F1/F3 (i.e., Caerin 1.1/Caerin 1.9) respectively on DAY 3; and the negative control group was injected with 100 μL of PBS solution every day for consecutive 7 days. B16 tumor tissues were taken and treated into single cell suspensions on DAY 13 for flow staining and detected by using a flow cytometer. Selected antibodies were as follows: FITC-CD45.2, Percp-cy5.5-CD11b, APC-Ly6G, BV421-Ly6c, FVS510 dye, and PE-F4/80. A modeling method was the same as above, splenic organs of mice were taken and processed into single cell suspensions on DAY 13, m-MDSC was sorted by using a flow cytometer, and four groups were set up: a PBS group, a PBS+GMCSF group, an F(F1/F3) group, and an F(F1/F3)+GMCSF group. The sorted cells were counted, each group was provided with two multiple wells, with 100,000 cells each well, 10 ng/ml of GMCSF was added to each group, and after three days of stimulating culture, the cells were detected by using the flow cytometer. Selected antibodies were as follows: FITC-CD45.2, Percp-cy5.5-CD11b, APC-Ly6G, BV421-Ly6c, FVS510 dye, and PE-F4/80.
3. Experimental results: There are two independent experiments, and latest experimental results were shown. The experimental results were shown in FIG. 6. In FIG. 6, A represented a proportion of macrophages in CD45.2+ cells; B represented a proportion of MDSC in CD45.2+ cells; C represented a proportion of m-MDSC in MDSC; and D represented a proportion of PMN-MDSC in MDSC. From this, it can be seen that: tumor macrophages after polypeptide therapy had a rising trend, which was consistent with the previous results. In addition, the proportion of MDSC, m-MDSC and PMN-MDSC tended to decrease, indicating that polypeptides can also achieve the purpose of promoting tumor immunity by reducing the proportion of myeloid-derived suppressor cells, as shown in the results of subsequent sorting in vitro stimulation culture experiments (FIG. 7). In FIG. 7, two figures of A and B showed typical flow charts of the proportion of macrophages in CD45.2 positive cells in the two groups under the condition that no stimulant is added or a stimulant is added, and the figure C represented a columnar statistical chart of the proportion of macrophages in CD45.2+ cells after the stimulant is added. Combined with the phenomenon that m-MDSC did not differentiate into macrophages with no GMCSF stimulant added in Figure A, it can be known that: compared with the PBS group, m-MDSC obtained by splenic organ sorting in the F1/F3 treatment group had more macrophages after GMSCF stimulus differentiation, and it was preliminarily proved in vitro that m-MDSC was differentiated into macrophages after polypeptide treatment.

Experiment Example 5 F1/F3 Combined with α-PD-1 for Treatment of Melanoma

Figure 8:
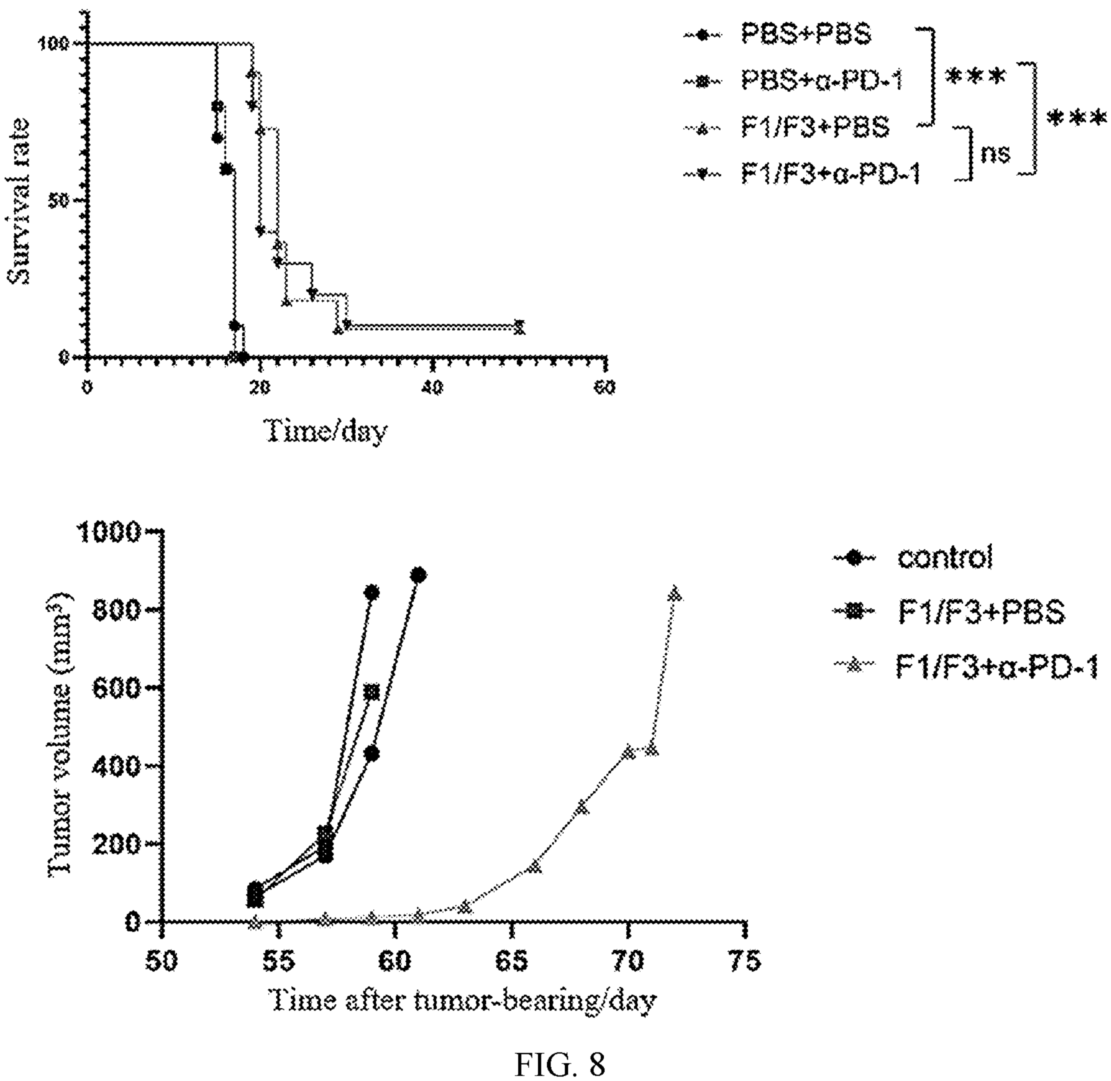
FIG. 8 shows a result of F1/F3 combined with α-PD-1 (an anti-programmed death receptor 1) for treating melanoma.

1. Experimental process: Time of subcutaneous inoculation of $4\times10^5$ B16 cells into the lateral abdomen of C57BL/6 mice was recorded as DAY 0. When tumors can be clearly observed (DAY 3), they were usually divided into four groups: a PBS+PBS group, a PBS+α-PD-1 group, an F(F1/F3)+PBS group, and an F(F1/F3)+α-PD-1 group, with 10 mice in each group. According to grouping requirements, 100 μL of PBS solution containing 30 μg of F1/F3 and PBS solution were injected into the tumor for 7 consecutive days; and then PBS solution containing 200 μg of α-PD-1 and PBS solution were injected intraperitoneally on DAY 9 and DAY 15 respectively. Cured mice were subcutaneously inoculated with $4\times10^5$ B16 cells on the other lateral abdomen for tumor re-stimulation on DAY 43, and at the same time, a same number of C57 mice were inoculated with a same number of B16 cells on the other lateral abdomen as a control group.
2. Experimental results: Specific experimental results were shown in FIG. 8. Compared with F1/F3 alone therapeutic strategies, the combined immunotherapy of F1/F3 and α-PD-1 did not prolong the survival time of mice, but the tumor prognosis of mice treated with combined immunotherapy was better than that of F1/F3 alone.

Figure 9:
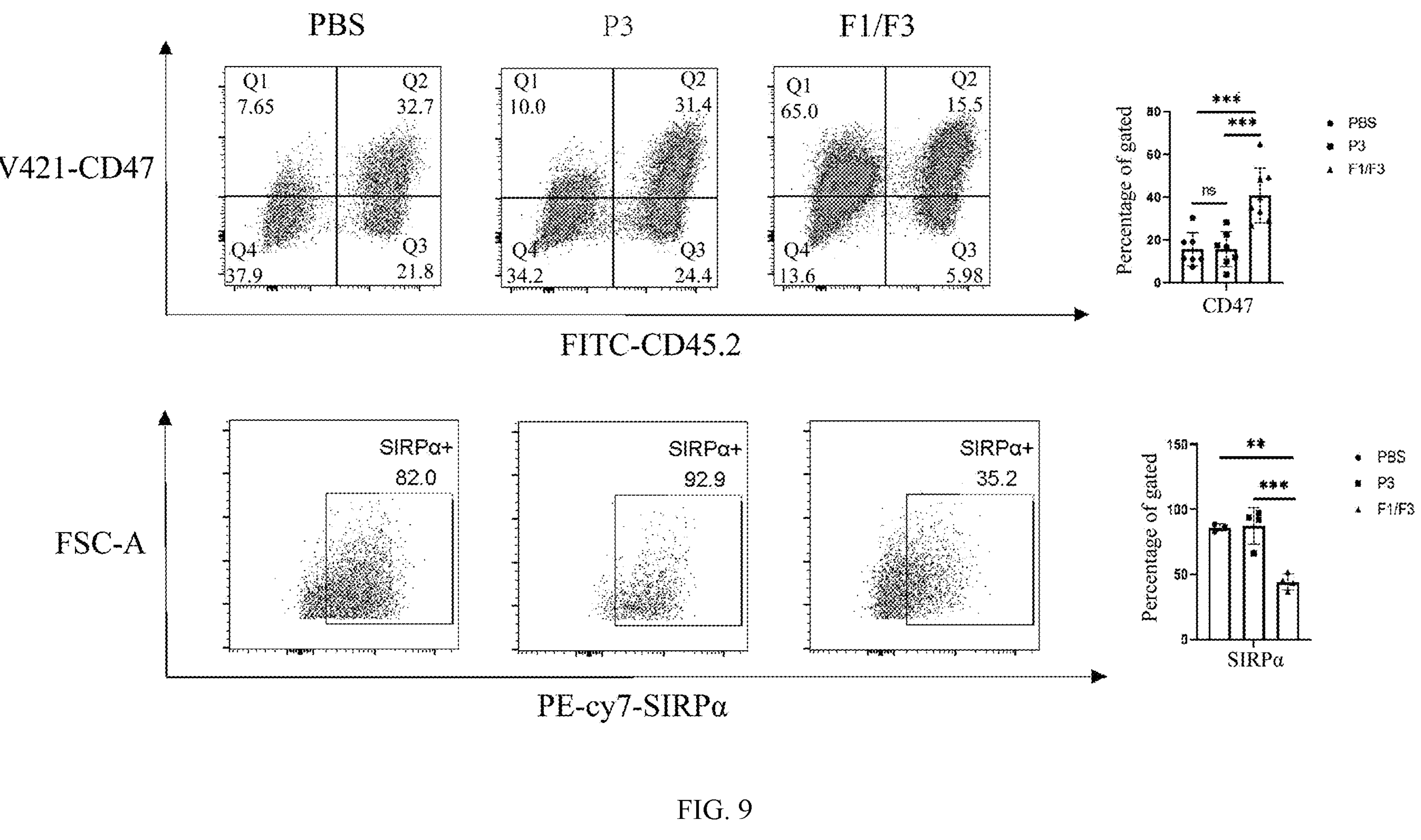
FIG. 9 shows a result of promoting the increase of CD47 by combined use of F1/F3.

Experiment Example 6 Changes Of Increase In CD47 Expression In F1/F3 Combined Treatment Of Model 1. Experiment objects: 21 C57BL/6 mice were divided into 3 groups with 7 mice in each group.
2. Experiment method: A modeling method was the same as that in Experiment example 3, the experiment was divided into a PBS group, a P3 group and an F1/F3 group, tumor tissues were taken and treated into single cell suspensions on DAY 13 for flow staining and detected by using a flow cytometer, two experiments were carried out continuously, and flow antibodies were selected as follows: FITC-CD45.2, FVS510 dye, and BV421-CD47.
3. Experimental results: This is a summary of results of two independent experiments, and the specific experimental results were shown in FIG. 9. In FIG. 9, although tumor growth was inhibited after polypeptide treatment, the expression of CD47 on tumor cells in the treatment group increased obviously, which indicated that tumor cells still sent out a signal of "Don't eat me" during the treatment, realizing immune escape, which provided a certain theoretical basis and feasibility for subsequent treatment of melanoma by Caerin 1.1/Caerin 1.9 combined with anti-CD47. Meanwhile, it was found that the expression of SIRPα on macrophages decreased, which indicated that the immune microenvironment after polypeptide treatment was inhibiting the occurrence of immune escape of tumor cells. This result provided a theoretical basis for subsequent triple therapy of melanoma with F1/F3, the therapeutic vaccine, and anti-CD47.

Experiment Example 7 F1/F3 Combined With CD47 for Treatment of Melanoma

Figure 10:
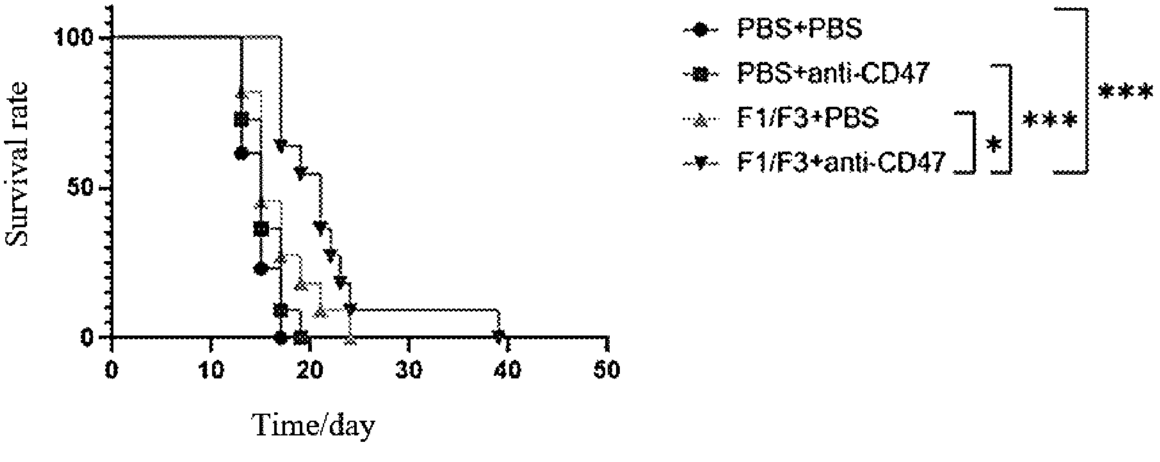
FIG. 10 shows a result of F1/F3 combined with anti-CD47 for treating melanoma.

1. Experimental process: Time of subcutaneous inoculation of $4\times10^5$ B16 cells into the lateral abdomen of C57BL/6 mice was recorded as DAY 0. When tumors can be clearly observed (DAY 3), they were usually divided into four groups: a PBS+PBS group, a PBS+anti-CD47 group, an F+PBS group, and an F+anti-CD47 group, with 6 mice in each group. According to grouping requirements, PBS solution containing 30 μg of F1/F3 and PBS solution were injected intratumorally and PBS solution containing 200 μg of anti-CD47 and PBS solution were injected intraperitoneally for 7 consecutive days from DAY 3. After that, 100 μg of anti-CD47 was injected intraperitoneally every other day until the end of the experiment, with all the volume of 100 μL.
2. Experimental results: Specific experimental results were shown in FIG. 10, which were comprehensive results of two independent experiments. Compared with F1/F3 alone or anti-CD47 alone, the immune combination therapy of F1/F3 and anti-CD47 significantly prolonged the survival time of mice.

Figure 11:
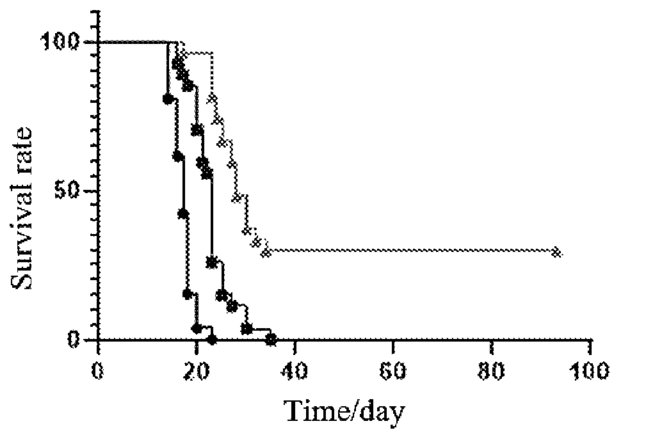
FIG. 11 shows a result of a cell survival rate of F1/F3 combined with α-PD-1 and a therapeutic vaccine for treating melanoma.
Figure 12:
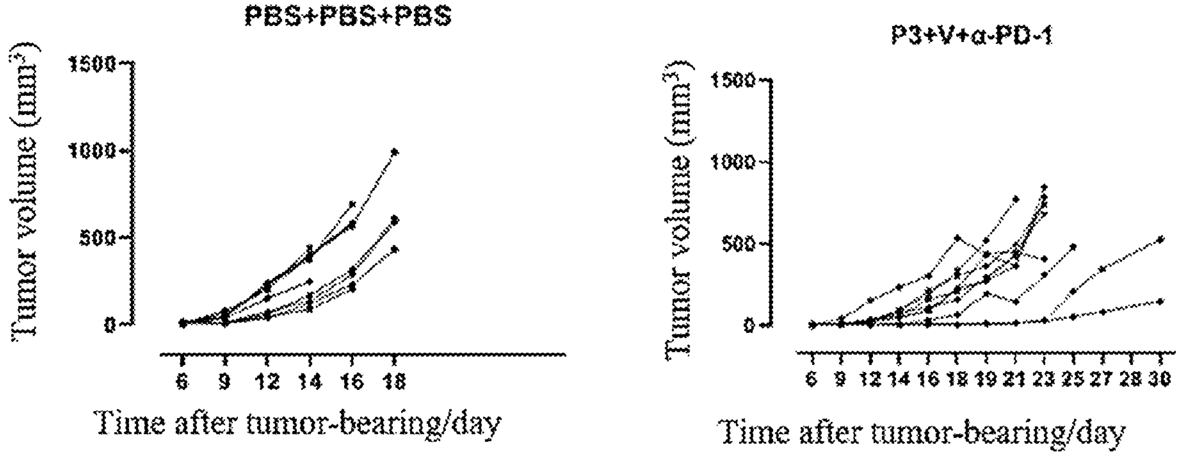
FIG. 12 shows a result of changes in tumor volume.
Figure 12:
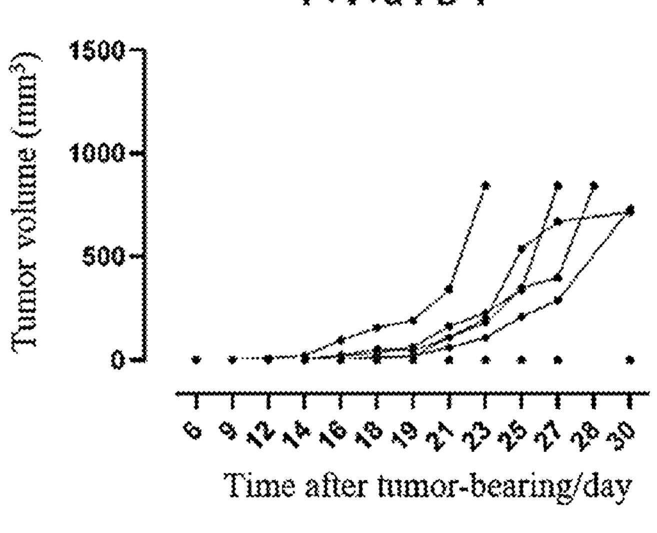

Experiment Example 8 F1/F3 Combined With α-PD-1 and Therapeutic Vaccine for Treatment of Melanoma 1. Experimental process: Time of subcutaneous inoculation of $4\times10^5$ B16 cells into the lateral abdomen of C57 mice was recorded as DAY 0; when tumors can be clearly observed (DAY 3), they were usually divided into three groups: a PBS+PBS+PBS group, a P3+V+α-PD-1 group, and an F1/F3+V+α-PD-1 group. PBS solution, PBS solution containing 30 μg of F1/F3, or PBS solution containing 30 μg of P3 (negative control) were intratumorally injected for 7 consecutive days respectively, with all the volume of 100 μL. 300 μg of α-PD-1 was injected intraperitoneally on DAY 9 and DAY 21 respectively, and a therapeutic vaccine was injected intramuscularly on DAY 3, Day 9 and Day 18 (V consisted of three components: melanoma therapeutic vaccine 50 μg/mouse, MPLA 15 μg/mouse, and α-IL10r 300 μg/mouse, with an average weight of 16-20 g per C57 mouse), which were repeated three times continuously.
2. Experimental results: Specific experimental results were shown in FIG. 11, which is the summation of three independent experiments. Results of tumor volume change were shown in FIG. 12, and the latest experimental results of three independent experiments were shown. It can be seen from FIG. 12 that the survival time of mice after triple therapy had been greatly prolonged, and nearly half of tumors of the mice had been completely eliminated. Compared with the PBS+PBS+PBS group and the P3+V+α-PD-1 group, there was a significant difference. The survival time of the P3+V+α-PD-1 group was significantly longer than that of the PBS+PBS+PBS group, which shows the feasibility of the triple therapy based on F1/F3, α-PD-1, and the therapeutic vaccine, and provides a theoretical basis for subsequent triple immunotherapy of anti-CD47.

Experiment Example 9 Study on Changes of Immune Microenvironment in Triple Therapy 1. Experimental process: A modeling method was the same as that in Experiment example 8. Tumor tissues were taken and treated into single cell suspensions on DAY 23 for flow staining and detected by using a flow cytometer. Selected flow antibodies were as follows: FITC-CD45.2, APC-cy7-CD3c, Percp-cy5.5-CD4, PE-cy7-CD8a, PE-NK1.1, PE-F4/80, Percp-cy5.5-CD11b, APC-Ly6C, BV421-CD56, BV421-MHCII, PE-CY7-CD86, and FVS510 dye.

Figure 13:
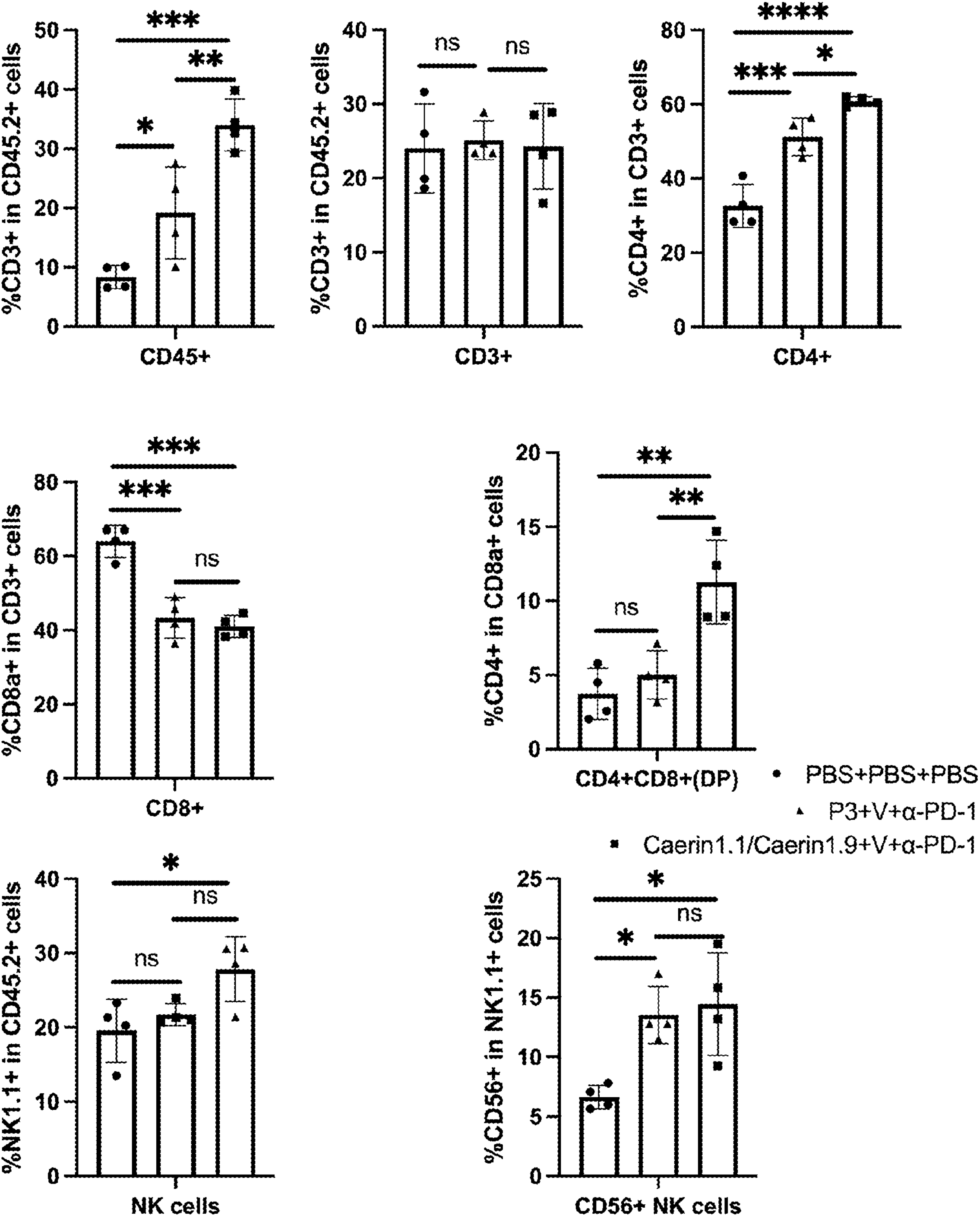
FIG. 13 and FIG. 14 show results of study and analysis of immune microenvironment changes in triple therapy.
Figure 14:
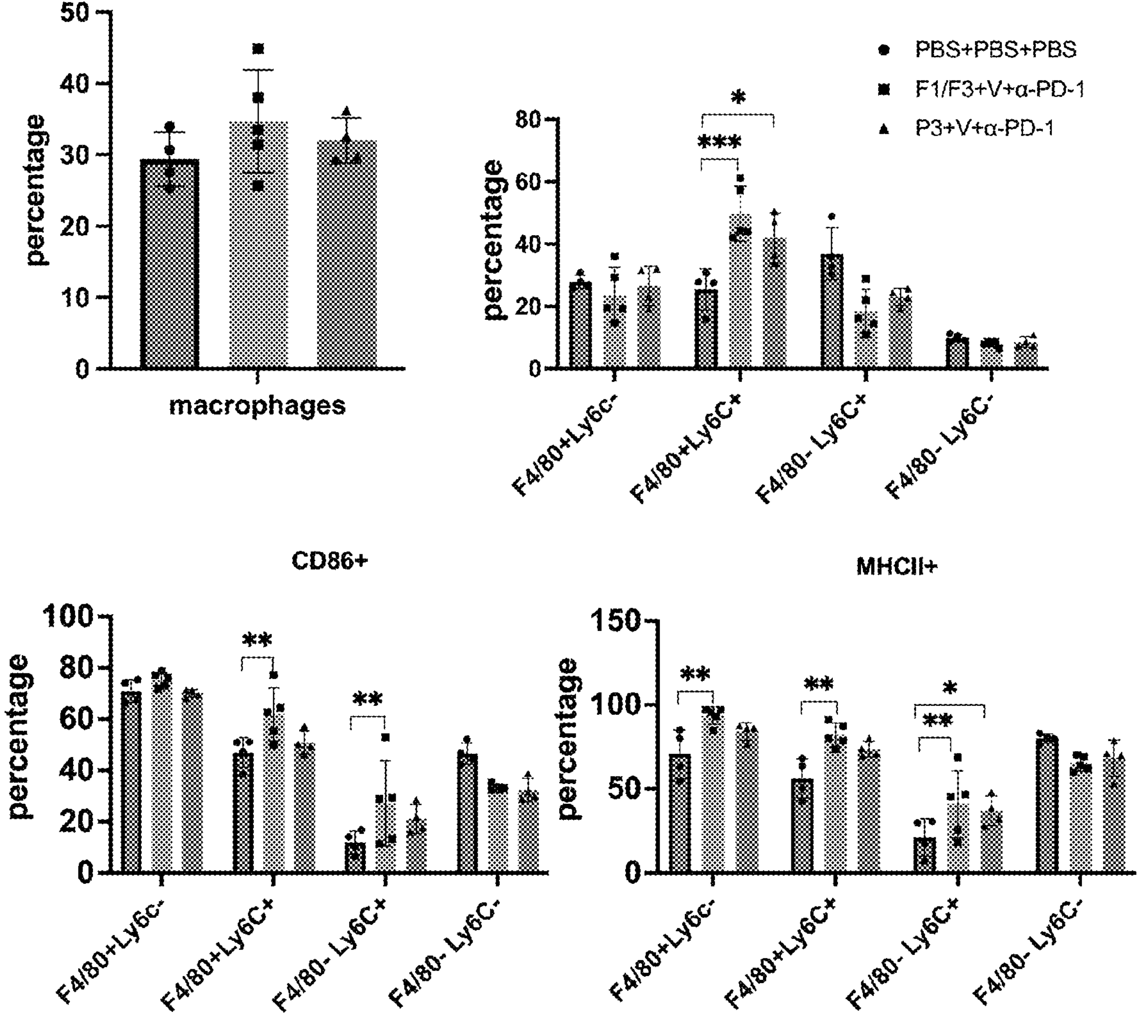

2. Experimental results: The experimental results were shown in FIG. 13 to FIG. 14. Compared with the other two groups, the proportion of CD4+T cells, DP T cells and CD56+NK cells in the F1/F3+V+α-PD-1 group increased, which indicates that triple therapy can better promote tumor immunity than dual therapy. Meanwhile, the results also showed that both CD86+macrophages and MHC II+macrophages had an increase in the proportion of Ly6c+subsets, which was consistent with the results of polypeptide therapy alone. It was preliminarily judged that the triple therapy also played a major role through macrophages.

Experiment Example 10 F1/F3 for Treatment of Nude Mice Bearing Tumor Model

Figure 15:
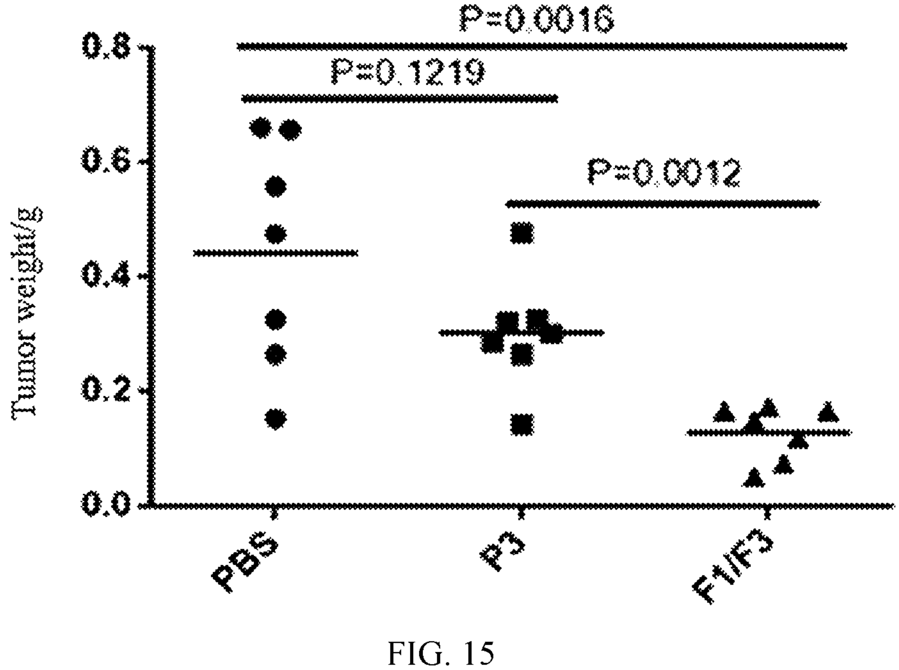
FIG. 15 shows a result of F1/F3 for treating a nude mice bearing tumor model.

1. Experimental process: A modeling method was the same as that in Experiment example 8. Mice were divided into three groups: a PBS group, a P3 group, and an F1/F3 group. Time of subcutaneous inoculation of $5\times10^5$ B16 cells into the lateral abdomen of nude mice was recorded as DAY 0. According to the groups, 100 μl of PBS solution containing 30 μg of F1/F3, PBS solution containing 30 μg of P3, and PBS solution were injected intratumorally for 7 consecutive days from DAY 3 respectively. The mice were killed on DAY 13 and the tumor was weighed.
2. Experimental results: Specific experimental results were shown in FIG. 15. The survival time of tumor-bearing nude mice was significantly prolonged after F1/F3 treatment.

Figure 16:
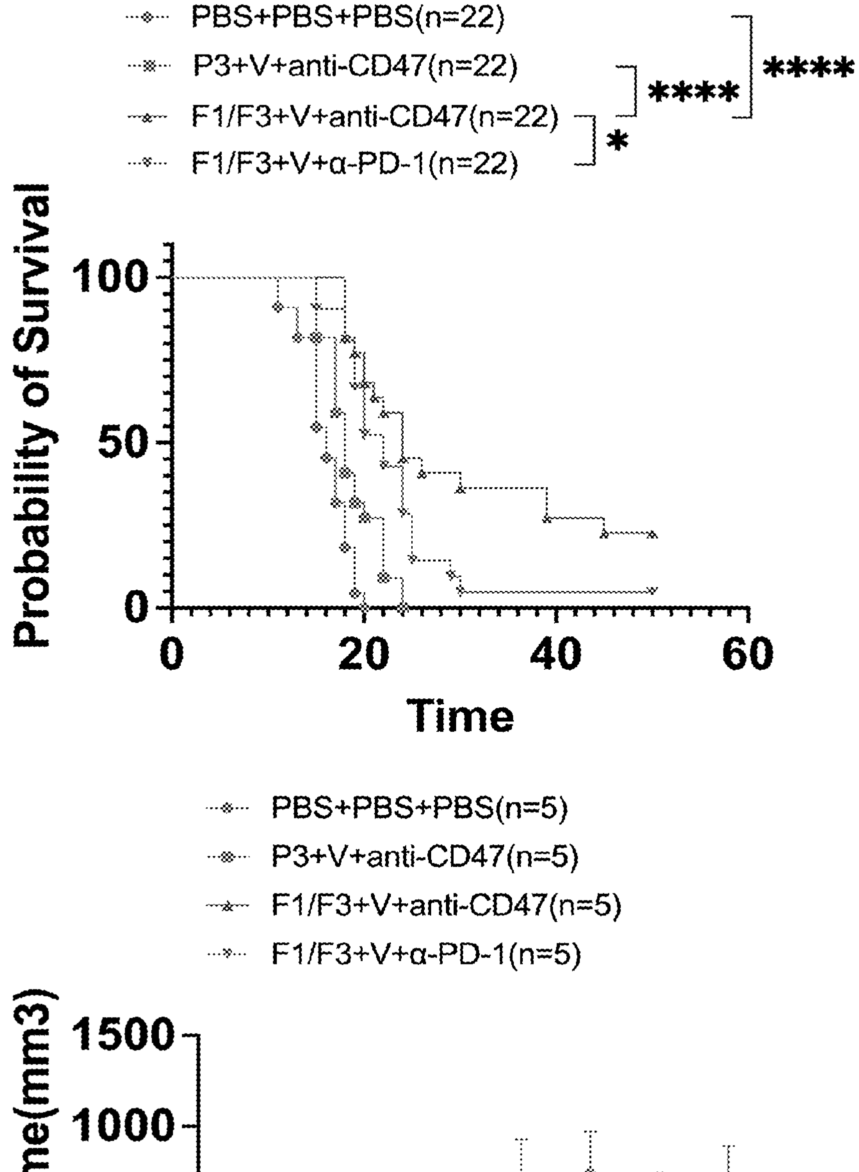
FIG. 16 shows a result of F1/F3 combined with anti-CD47 and a therapeutic vaccine for treating melanoma.

Experiment Example 11 F1/F3 Combined with Anti-CD47 and Therapeutic Vaccine for Treatment of Melanoma 1. Experimental process: Time of subcutaneous inoculation of $4\times10^5$ B16 cells into the lateral abdomen of C57 mice was recorded as DAY 0. When tumors can be clearly observed (DAY 3), they were usually divided into four groups: a PBS+PBS+PBS group, a P3+V+anti-CD47 group, an F1/F3+V+anti-CD47 group, and an F1/F3+V+α-PD-1 group. PBS solution, PBS solution containing 30 μg of F1/F3 or PBS solution containing 30 μg of P3 (negative control) were intratumorally injected for 7 consecutive days respectively, with all the volume of 100 μL. In the F1/F3+V+α-PD-1 group, PBS solution containing 300 μg of α-PD-1 was injected intraperitoneally on DAY 9 and DAY 21 respectively, with a volume of 100 μL. In the P3+V+anti-CD47 group, the F1/F3+V+anti-CD47 group, and the F1/F3+V+α-PD-1 group, 100 μL of the therapeutic vaccine were injected intramuscularly on DAY 3, Day 9 and Day 18 (V consisted of three components: melanoma therapeutic vaccine 50 μg/mouse, MPLA 15 μg/mouse, and α-IL10r 300 μg/mouse, with an average weight of 16-20 g per C57 mouse), which were repeated three times continuously. The other groups were injected with 100 μL of PBS. Each mouse in the P3+V+anti-CD47 group and the F1/F3+V+anti-CD47 group was intraperitoneally injected with PBS solution containing 200 μg of anti-CD47 on DAY 3, with a volume of 100 μL, once every other day, and the other groups were intraperitoneally injected with 100 μl of PBS as control until the end of the experiment.
2. Experimental results: Specific experimental results were shown in FIG. 16. It may be seen from the figure that the triple therapy based on F1/F3 combined with the anti-CD47 and the therapeutic vaccine had better effect of treating melanoma than the therapy based on F1/F3 combined with the α-PD-1 and the therapeutic vaccine, and the dual therapy can also inhibit the growth of tumor, but its therapeutic effect is not as good as that of the triple therapy. The above description shows that replacing α-PD-1 with anti-CD47 can better inhibit tumor growth and improve the therapeutic effect of the triple therapy.

Finally, it should be noted that the above embodiments are only intended to exemplarily illustrate the principle, performance, and effect of the present invention but not intended to limit the present invention. Any person of ordinary skill in the art can modify or change the above examples without departing from the spirit and scope of the present invention. Therefore, all equivalent modifications or changes made by those of ordinary skill in the art without departing from the spirit and technical ideal disclosed by the present invention should still fall within the claims of the present invention.

What is claimed is:

1. A method of treating melanoma in a subject, comprising:

administering to the subject Caerin 1.1/1.9 and an anti-CD47 antibody clone MIAP301;

wherein a mass ratio of the Caerin 1.1/1.9 to the anti-CD47 antibody is 3: (10-25);

the Caerin 1.1/1.9 consists of Caerin 1.1 and Caerin 1.9 according to a mass ratio of 1:1;

an amino acid sequence of the Caerin 1.1 is shown in SEQ ID NO.1; and an amino acid sequence of the Caerin 1.9 is shown in SEQ ID NO.2.

2. The method according to claim 1, wherein the drug further comprises a pharmaceutically acceptable carrier.

3. A method of inducing melanoma cells B16 to highly express CD47, comprising:

treating the melanoma cells B16 with Caerin 1.1/1.9;

wherein the Caerin 1.1/1.9 consists of Caerin 1.1 and Caerin 1.9 according to a mass ratio of 1:1; an amino acid sequence of the Caerin 1.1 is shown in SEQ ID NO.1; and an amino acid sequence of the Caerin 1.9 is shown in SEQ ID NO.2.

4. The method according to claim 1, wherein the step of administering Caerin 1.1/1.9 and the anti-CD47 antibody clone MIAP301 results in repolarization of tumor-infiltrating macrophages from an M2 type to an M1 type.

5. The method according to claim 4, wherein the step of administering Caerin 1.1/1.9 and the anti-CD47 antibody clone MIAP301 results in increased interleukin-12 secretion and decreased interleukin-10 secretion.

6. The method according to claim 5, wherein the step of administering Caerin 1.1/1.9 and the anti-CD47 antibody clone MIAP301 results in increased expression of CD47 on melanoma cells.

* * * * *